United States Patent [19]

Cowie

[11] Patent Number: 5,588,440
[45] Date of Patent: Dec. 31, 1996

[54] METHOD AND APPARATUS FOR LOCATING AND ASSESSING SOFT TISSUE LESIONS

[76] Inventor: Jocelyn W. Cowie, P.O. Box 1495, 6700 Danshin Village Road, Grand Forks, B.C., Canada, V0H 1H0

[21] Appl. No.: 513,406

[22] Filed: Aug. 10, 1995

[51] Int. Cl.⁶ ..................................................... A61B 5/05
[52] U.S. Cl. ........................................ 128/734; 128/773
[58] Field of Search ..................................... 128/773, 734, 128/744, 737, 736

[56] References Cited

U.S. PATENT DOCUMENTS

| | | | |
|---|---|---|---|
| 2,829,638 | 4/1958 | Douglas | 128/734 |
| 4,966,158 | 10/1990 | Honma et al. | 128/734 |
| 5,233,515 | 8/1993 | Cosman | 128/734 |
| 5,301,679 | 4/1994 | Taylor | 128/773 |

FOREIGN PATENT DOCUMENTS

| | | | |
|---|---|---|---|
| 1254269 | 5/1989 | Canada | A61B 5/05 |
| PCT9001991 | 7/1991 | WIPO | A61B 5/05 |

*Primary Examiner*—Max Hindenburg
*Assistant Examiner*—Pamela L. Wingood

[57] ABSTRACT

A method and apparatus for locating and assessing soft tissue lesions includes a probe for contacting an area of skin. The probe includes means for measuring the moisture content of the skin and means for measuring sound generated by the skin. A lesion is indicated by a moisture content and a sound reading that are both abnormally high. The probe can also include means for measuring the temperature of the skin for detecting a lesion by elevated temperature.

8 Claims, 2 Drawing Sheets

METHOD AND APPARATUS FOR LOCATING AND ASSESSING SOFT TISSUE LESIONS

FIELD

The present method relates to a method and apparatus for assessing and locating soft tissue lesions manifested by pain in the tissue of human beings and animals.

BACKGROUND

It is known that the electrical resistance of skin is controlled largely through the nervous system. Canadian Patent No. 1,254,269 issued May 16, 1989 to Woodley et al. discloses a diagnostic device based upon resistance measurements of the skin which is used to detect abnormal areas of the body where there is pain or sympathetic disfunction. U.S. Pat. No. 4,966,158 issued to Honma et al. discloses a device having two probes which measures the moisture content retained in the skin both in the keratinous layer and also in the deeper layer so as to provide information as to the condition of the skin. Patent Cooperation Treaty Application No. PCT/GB90/01991 discloses a device having a common probe and a reference probe. The measurement of resistance is switched between a common probe applied to an area of skin under test and a reference probe located on the identical area on the other side of the body. A difference in the readings indicates a damaged area of the skin. Thus, known devices measure only one parameter of the skin.

In order to be able to cross correlate different types of measurements of a given area and thus obtain confirmation of the condition and a more accurate diagnosis, it would be useful to be able to measure several different parameters simultaneously. Technically, one could first apply a device to measure resistance to a particular area and then one designed to measure moisture. However, such an approach would be impractical because not only could the condition of the area under test change from one measurement to the other, but positioning the probe on precisely the same area for both measurements would be difficult if not impractical. Secondly, many such measuring devices require measurements to be made using two separate probes applied to two separate but corresponding sides of the body.

Accordingly, it is an object of the invention to provide a method and apparatus for simultaneously measuring at least two different parameters of the skin.

SUMMARY OF THE INVENTION

Cellular damage can occur due to prolonged stress, which increase build-up of metabolites and tissue ischemia. The latter build-up directly excites pain receptors and causes cellular degeneration or necrosis. Lack of use, poor posture, over use, a blow or hyperextension will cause lesions resulting in inflammation. Inflammation products such as histamine, bradykinin, acids, etc. are released into the capillary bed and produce pain. Pain causes a reflex response of muscle guarding and/or spasms. Such a response leads to immobility and eventual wasting away or atrophy due to loss of the alternating relaxing and contracting of muscles. The muscles provide a circulatory pumping action during normal relaxation and contracting which will be ineffective on areas affected by atrophy. Ordinarily, painful areas in the skin are associated with abnormalities such as changes in temperature, and moisture, tenderness, swelling or edema, inflammation, stringiness due to fibrous tissue changes, nodules or small knotted areas, fatigue or lack of tone in the tissues, and metabolite retention characterized by crystal-like formations in the tissue. Such areas of abnormality are conventionally located by a palpative process.

Manual compressions such as applied by accupressure or massage, remove the stimuli causing pain and stopping stimulation of the sweat glands and arterial vessel constriction, the primary cause of pain and degenerative tissue disorders. Such compression and massage are accompanied by the sound of the breaking up processes of metabolite and tissue by-products. Thus, factors such as moisture, sound, temperature, electrical conductivity, edema are all a function of the condition of the skin and can be used to measure tile presence of areas of pain or lesions.

According to the invention there is provided apparatus for diagnosing the skin condition of a human being or animal, which includes a probe for contacting a desired area of skin. The probe has means for measuring the moisture content of the skin at the area and means for measuring the sound produced during massage of the skin at that area.

A tip of said probe may be rounded and sufficiently small so that it will cause pitting due to edema when pressed against a damaged area of the skin.

The tip may also include means for measuring the temperature of the skin tissue at the area.

Means for measuring the moisture content may be a meter for measuring electrical resistance of the skin.

Means for measuring the sound may be a stethoscope which is incorporated into the probe having a sound receiving chamber proximate a tip of the probe.

Means for measuring temperature may include a thermocouple located proximate a tip of the probe.

In another aspect of the invention there is provided a method of locating and treating soft tissue lesions which includes passing a probe over the skin of a patient and measuring sound emanating from the skin so as to rapidly locate a pain producing area of the skin and measuring the resistance of the skin at the area. The method further includes massaging the pain producing area and simultaneously measuring the sound produced therefrom and applying massage to the area and then remeasuring the resistance and sound of the skin at the area to determine the amount of decrease thereof.

The method further measures the temperature at the point of contact of the skin with the probe.

BRIEF DESCRIPTION OF THE DRAWINGS

Further features and advantages will be apparent from the following detailed description, given by way of example, of a preferred embodiment taken in conjunction with the accompanying drawings, wherein.

DETAILED DESCRIPTION WITH REFERENCE TO THE DRAWINGS

Figure 1:
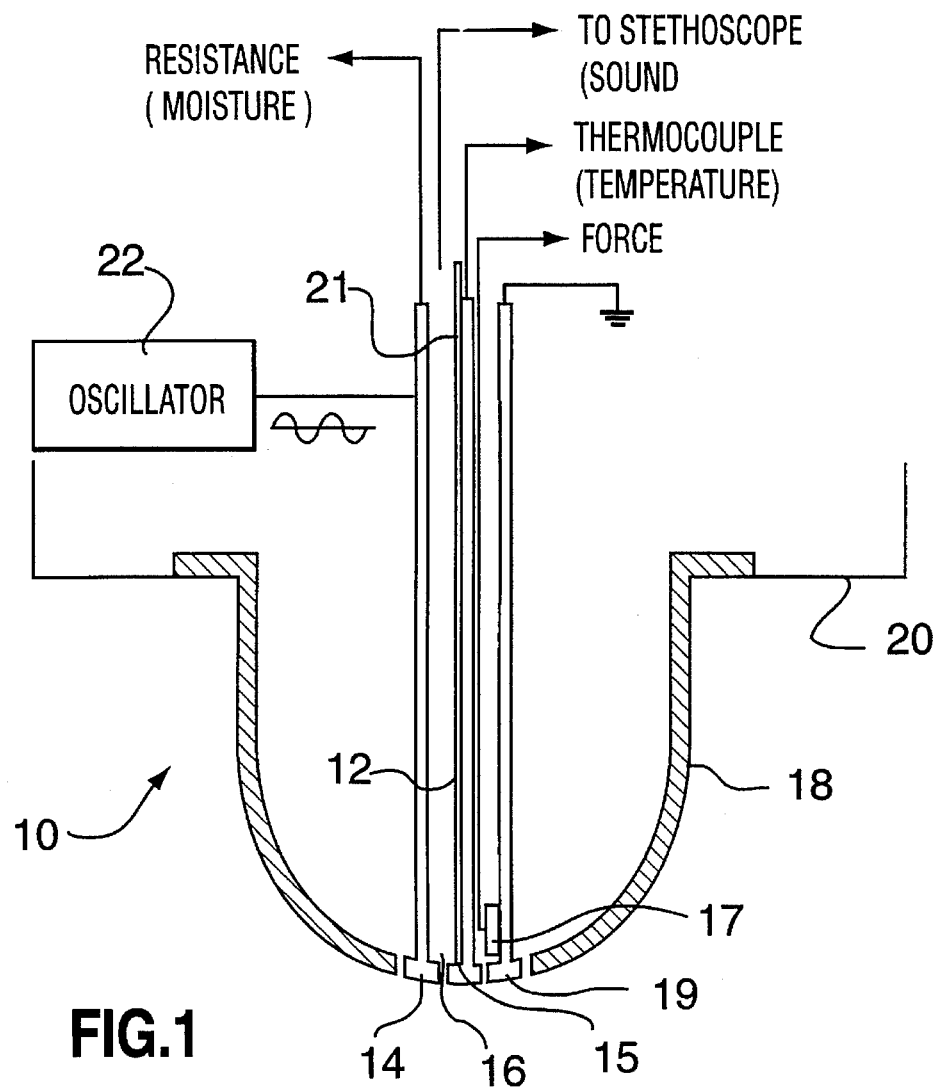
FIG. 1 is a sectional elevation view of the probe of an instrument for measuring temperature, sound, moisture and applied force.
Figure 2:
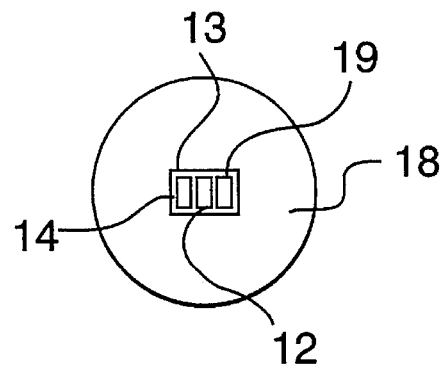
FIG. 2 is a top view of the probe shown at a reduced scale from that of FIG. 1.

Referring to FIGS. 1 and 2 there is shown a probe 10 having a generally semi-circular cross-section from the tip back to the casing 20 and an rectangular opening 13 through which there protrudes three sensors 14, 12 and 19. An open area 16 around the sensors serves to conduct sound up to a sound detector or stethoscope (not shown) of conventional design.

A galvanometer junction 15 is located at the end of sensor 12. The leads 21 from the galvanometer junction 15 run up to a meter (not shown) which displays the temperature of the junction 15.

Sensor 19 has a two-fold function. It acts as a ground terminal in conjunction with terminal 14 as well as providing strain to transducer 17 to allow the latter to measure applied force. The applied force provides a useful objective measure of the force being applied with the probe 10.

In operation, the moisture meter component of the probe 10 is formed by oscillator 22, conductive element 14, conductive element 19 and amplifier, filter, rectifier and an analog to digital converter as shown in U.S. Pat. No. 4,966,158 which is incorporated herein by reference.

The simultaneous development of signals which correspond to moisture content, temperature and sound allow all three of these factors to be cross correlated to confirm an indicated condition by any one of them and to more accurately define the nature and extent of the condition. The pressure indicator allows a user to monitor and control the amount of pressure being applied. One may determine the pressure required to cause pitting edema, another sign of lesions.

Figure 3:
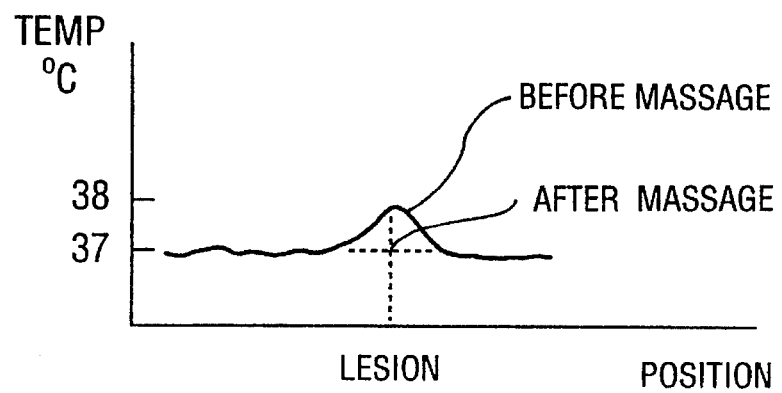
FIG. 3 is is a graph of temperature versus position of the probe.
Figure 4:
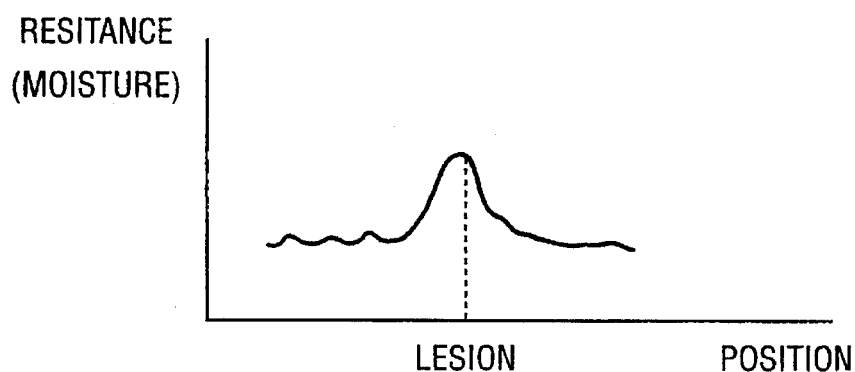
FIG. 4 is a graph of electrical resistance as a function of the position on the skin.
Figure 5:
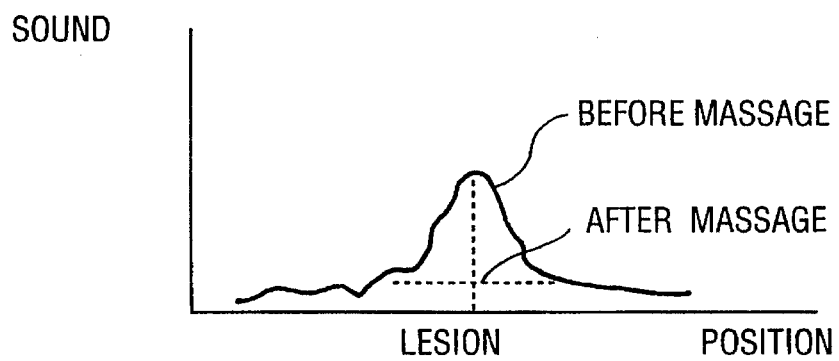
FIG. 5 is a graph of the sound emitted by the skin during massage with the probe as a function of position on the skin.

FIGS. 3 to 5 shows graphs of the readings of temperature, resistance, and sound as one progresses towards, over and then away from a lesion. The same Figures show readings of the same lesion after applying massage (see the dotted lines). Thus, the probe allows the massage therapist to determine the effect of the massage on a lesion to a quantifiable extent. A therapist can use the sound output to rapidly locate suspected damaged areas of the skin and then to confirm the damage using the other readings of temperature, moisture content and resistance. Any extraneous readings in any one or more of the factors of temperature, moisture, and sound can be checked as to their origin by comparing them to the readings for the other factors.

Accordingly, while this invention has been described with reference to illustrative embodiments, this description is not intended to be construed in a limiting sense. Various modifications of the illustrative embodiments, as well as other embodiments of the invention, will be apparent to persons skilled in the art upon reference to this description. It is therefore contemplated that the appended claims will cover any such modifications or embodiments as fall within the true scope of the invention.

I claim:

1. Apparatus for diagnosing the skin condition of a human being or animal, comprising a probe for contacting a desired area of skin, said probe having
   (a) means for measuring the moisture content of the skin at said area; and
   (b) means for measuring the sound generated by the skin tissue in said area;
   wherein said means for measuring the moisture content and said means for measuring sound indicate the presence of skin lesion when the moisture content and the sound reading are both abnormally high.

2. Apparatus according to claim 1, wherein a tip of said probe is rounded and sufficiently small so that it will cause pitting due to edema when pressed against a damaged area of the skin.

3. Apparatus according to claim 1, including means for measuring the temperature of the skin tissue at said area.

4. Apparatus according to claim 1, wherein said means for measuring the moisture content is a meter for measuring the electrical resistance of the skin.

5. Apparatus according to claim 3, wherein said means for measuring the sound is a stethoscope which is incorporated into said probe having a sound receiving chamber proximate a tip of said probe.

6. Apparatus according to claim 1, wherein said means for measuring temperature includes a thermocouple located proximate a tip of said probe.

7. A method of locating and treating pain, comprising the steps of:
   (a) passing a probe over the skin of a patient and measuring sound emanating from the skin so as to rapidly locate a soft tissue lesion of the skin,
   (b) measuring the resistance of the skin at said area to verify the presence of said lesion;
   (c) massaging said lesion with said probe and simultaneously measuring the sound produced by said lesion to monitor the reduction in sound due to massaging;
   (d) applying manual massage to said area; and
   (e) re-measuring the resistance and sound of the skin at said area to determine the amount of decrease thereof;
   whereby a sound reduction verifies the presence of a lesion and re-measuring provides an indication of the effectiveness of treating the lesion.

8. A method according to claim 7, including measuring the temperature at the point of contact of the skin with the probe.

\* \* \* \* \*